United States Patent
Chen et al.

(10) Patent No.: US 11,330,970 B2
(45) Date of Patent: May 17, 2022

(54) FLEXIBLE HIGH RESOLUTION ENDOSCOPE

(71) Applicant: SYNAPTIVE MEDICAL INC., Toronto (CA)

(72) Inventors: Sean Jy-Shyang Chen, Toronto (CA); Kamyar Abhari, Toronto (CA); Michael Frank Gunter Wood, Toronto (CA); Gal Sela, Toronto (CA)

(73) Assignee: SYNAPTIVE MEDICAL INC., Toronto (CA)

( * ) Notice: Subject to any disclaimer, the term of this patent is extended or adjusted under 35 U.S.C. 154(b) by 637 days.

(21) Appl. No.: 16/326,349

(22) PCT Filed: Aug. 17, 2016

(86) PCT No.: PCT/IB2016/054931
§ 371 (c)(1),
(2) Date: Feb. 18, 2019

(87) PCT Pub. No.: WO2018/033775
PCT Pub. Date: Feb. 22, 2018

(65) Prior Publication Data
US 2019/0223704 A1    Jul. 25, 2019

(51) Int. Cl.
*A61B 1/00* (2006.01)
*A61B 1/045* (2006.01)
(Continued)

(52) U.S. Cl.
CPC .............. *A61B 1/045* (2013.01); *A61B 1/005* (2013.01); *A61B 1/0051* (2013.01); *A61B 1/04* (2013.01); *A61B 1/07* (2013.01); *G02B 23/2415* (2013.01); *G02B 23/2469* (2013.01); *A61B 1/01* (2013.01); *A61B 1/0676* (2013.01)

(58) Field of Classification Search
None
See application file for complete search history.

(56) References Cited

U.S. PATENT DOCUMENTS 4,480,636 A * 11/1984 Karaki ............... G02B 23/2484
600/109
5,459,605 A * 10/1995 Kempf ............... A61B 1/00165
359/462

(Continued)

OTHER PUBLICATIONS

Gaochang Wu et al., Light Field Image Processing: An Overview, IEEE Journal of Selected Topics in Signal Processing, Aug. 2017.

*Primary Examiner* — Timothy J Neal

(57) ABSTRACT

A flexible high resolution endoscope is provided herein. The endoscope comprises: a plurality of optical fiber bundles; a plurality of lenses in a one-to-one relationship with the plurality of optical fiber bundles; and, a plurality of cameras in a one-to-one relationship with the plurality of optical fiber bundles, each respective optical fiber bundle, of the plurality of optical fiber bundles, having a respective lens, of the plurality of lenses, located at a respective distal end, and a camera, of the plurality of cameras, located at a respective proximal end, the plurality of optical fiber bundles being coupled together at a common distal end, and otherwise being uncoupled from one another, a bending radius of the endoscope defined by a largest respective bending radius of each of the plurality of optical fiber bundles.

20 Claims, 13 Drawing Sheets

(51) Int. Cl.
  *A61B 1/07* (2006.01)
  *A61B 1/04* (2006.01)
  *A61B 1/005* (2006.01)
  *G02B 23/24* (2006.01)
  *A61B 1/01* (2006.01)
  *A61B 1/06* (2006.01)

(56) References Cited

U.S. PATENT DOCUMENTS

| | | | |
|---|---|---|---|
| 2005/0219552 A1* | 10/2005 | Ackerman | A61B 1/042 356/603 |
| 2007/0066869 A1* | 3/2007 | Hoffman | A61B 1/00135 600/121 |
| 2008/0015412 A1* | 1/2008 | Hori | A61B 1/00193 600/109 |
| 2010/0286475 A1* | 11/2010 | Robertson | A61B 1/00096 600/104 |
| 2012/0008017 A1* | 1/2012 | Jeong | H04N 5/3675 348/246 |
| 2013/0131447 A1* | 5/2013 | Benning | A61B 1/00101 600/109 |

* cited by examiner

FLEXIBLE HIGH RESOLUTION ENDOSCOPE

CROSS-REFERENCE TO RELATED APPLICATION(S)

This document is a national stage entry application claiming the benefit of, and priority to, International Application No. PCT/IB20176/054931, filed on Aug. 17, 2016, and entitled "A Flexible High Resolution Endoscope," which is hereby incorporated by reference in its entirety.

FIELD

The specification relates generally to medical imaging and methods for minimally invasive therapy and image guided medical procedures, and specifically to a flexible high resolution endoscope.

BACKGROUND

Traditional flexible endoscopes, also known as fibrescopes, allow for visualization during minimally invasive procedure. However, these fiberscopes produce two-dimensional images devoid of three-dimensional depth information, which is critical to a surgeon attempting to identify and operate on small or difficult to see structures. Images acquired by these state-of-the-art fiberscopes are also relative low in quality due to the limited resolution of the fibre bundle use to transmit the image to the sensor, with higher resolution image guides still much lower in resolution than current imaging standards. Typical fibre image guides provide images having a resolution of about 18 kilopixels compared to the megapixel resolutions displayed in high-definition video. Furthermore, while some higher resolution image guides are available, this higher resolution is achieved using thicker optical fiber-bundles than those used with typical fibre image guides, and hence higher resolution image guides are constrained in their bending, with much larger turning radii that limits where they can be used in a surgical case.

SUMMARY

The present disclosure is generally directed to image guided medical procedures using an access port. This port-based surgery approach allows a surgeon, or robotic surgical system, to perform a surgical procedure involving tumor resection in which the residual tumor remaining after is minimized, while also minimizing the trauma to the intact white and grey matter of the brain. In such procedures, trauma may occur, for example, due to contact with the access port, stress to the brain matter, unintentional impact with surgical devices, and/or accidental resection of healthy tissue.

Hence, an aspect of the present specification provides a flexible endoscope that can produce three-dimensional images, the endoscope comprising multiple fibre-bundle image guides (each of which can be around 18 kilopixels resolution), coupled to a multi-lens array on one end and multiple camera sensors on the other. The fibre-bundles in the endoscope are coupled together at a common distal end, and are otherwise uncoupled from one another. Each lens on the array projects a separate image to a different fiber-bundle at the distal scope end of each fibre-bundle, each of which respectively conveys a respective image to a respective camera sensor are coupled to an opposite proximal end of each fiber-bundle, such that the endoscope acquires a plurality of separate pixelated images. These images, acquired by each of the sensors, can then be merged and reconstructed using, for example, principles of light field imaging and processing, to produce a super-resolution image. This can allow for much higher resolution imaging than is possible with conventional fibrescopes, which can allow for better diagnosis and treatment. Furthermore, the endoscope provided herein can be more flexible than high resolution endoscopes as the flexibility is determined by each individual fiber-bundle which are coupled together only at a distal end.

An aspect of the specification provides an endoscope comprising: a plurality of optical fiber bundles; a plurality of lenses in a one-to-one relationship with the plurality of optical fiber bundles; and, a plurality of cameras in a one-to-one relationship with the plurality of optical fiber bundles, each respective optical fiber bundle, of the plurality of optical fiber bundles, having a respective lens, of the plurality of lenses, located at a respective distal end, and a camera, of the plurality of cameras, located at a respective proximal end, the plurality of optical fiber bundles being coupled together at a common distal end, and otherwise being uncoupled from one another, a bending radius of the endoscope defined by a largest respective bending radius of each of the plurality of optical fiber bundles.

The plurality of optical fiber bundles can comprise a first optical fiber bundle and a second optical fiber bundle, each having the respective lens located at the respective distal end, and the respective camera located at the respective proximal end, thereby forming a three-dimensional camera.

Respective distal ends of the plurality of optical fiber bundles, and respective lenses located at the respective distal ends, can be spaced apart from one another to provide different views of objects in front of the respective distal ends, thereby forming a plenoptic camera.

The plurality of lenses is each formed in a common optical element can be located at the common distal end.

The plurality of lenses can each be formed in a common optical element located at the common distal end, the common optical element being one or more of: removable from the common distal end of the plurality of optical fiber bundles; and disposable.

Two or more of the plurality of lenses can have one or more of: different depths of field, different fields of view of objects in front of the plurality of lenses: and different angular view of objects in front of the plurality of lenses.

The endoscope can further comprise a controller configured to: receive respective images from each of the plurality of cameras; and combine the respective images into a single higher resolution image.

The endoscope can further comprise a controller configured to: receive respective images from each of the plurality of cameras; remove dead pixels from the respective images; and combine the respective images into a single higher resolution image.

The endoscope can further comprise a controller configured to: receive respective images from each of the plurality of cameras; and combine the respective images into a depth-map of objects in front of the plurality of lenses.

The endoscope can further comprise a controller configured to: receive respective images from each of the plurality of cameras; and combine the respective images into a depth-map of objects in front of the plurality of lenses using light field processing.

Each respective diameter of the plurality of optical fiber bundles can be less than or equal to about 2 mm.

Another aspect of the specification provides a method comprising: at an endoscope having: a plurality of optical fiber bundles; a plurality of lenses in a one-to-one relationship with the plurality of optical fiber bundles; a plurality of cameras in a one-to-one relationship with the plurality of optical fiber bundles, each respective optical fiber bundle, of the plurality of optical fiber bundles, having a respective lens, of the plurality of lenses, located at a respective distal end, and a camera, of the plurality of cameras, located at a respective proximal end, the plurality of optical fiber bundles being coupled together at a common distal end, and otherwise being uncoupled from one another, a bending radius of the endoscope defined by a largest respective bending radius of each of the plurality of optical fiber bundles; and a controller configured to: receive respective images from each of the plurality of cameras, receiving, at the controller, the respective images from each of the plurality of cameras; combining, at the controller, the respective images into a single higher resolution image; and combining the respective images into a depth-map of objects in front of the plurality of lenses.

The method can further comprise: removing, at the controller, dead pixels from the respective images prior to combining the respective images into one or more of the single higher resolution image and the depth-map.

The method can further comprise: combining the respective images into the depth-map using a light field processing.

Two or more of the plurality of lenses have one or more of: different depths of field, different fields of view of objects in front of the plurality of lenses: and different angular view of objects in front of the plurality of lenses.

Yet a further aspect of the specification provides a computer-readable medium storing a computer program, wherein execution of the computer program is for: at an endoscope having: a plurality of optical fiber bundles; a plurality of lenses in a one-to-one relationship with the plurality of optical fiber bundles; a plurality of cameras in a one-to-one relationship with the plurality of optical fiber bundles, each respective optical fiber bundle, of the plurality of optical fiber bundles, having a respective lens, of the plurality of lenses, located at a respective distal end, and a camera, of the plurality of cameras, located at a respective proximal end, the plurality of optical fiber bundles being coupled together at a common distal end, and otherwise being uncoupled from one another, a bending radius of the endoscope defined by a largest respective bending radius of each of the plurality of optical fiber bundles; and a controller configured to: receive respective images from each of the plurality of cameras, receiving, at the controller, the respective images from each of the plurality of cameras; combining, at the controller, the respective images into a single higher resolution image; and combining the respective images into a depth-map of objects in front of the plurality of lenses. The computer-readable medium can comprise a non-transitory computer-readable medium.

BRIEF DESCRIPTIONS OF THE DRAWINGS

For a better understanding of the various implementations described herein and to show more clearly how they may be carried into effect, reference will now be made, by way of example only, to the accompanying drawings in which.

DETAILED DESCRIPTION

Various implementations and aspects of the specification will be described with reference to details discussed below. The following description and drawings are illustrative of the specification and are not to be construed as limiting the specification. Numerous specific details are described to provide a thorough understanding of various implementations of the present specification. However, in certain instances, well-known or conventional details are not described in order to provide a concise discussion of implementations of the present specification.

The systems and methods described herein may be useful in the field of neurosurgery, including oncological care, neurodegenerative disease, stroke, brain trauma and orthopedic surgery; however persons of skill will appreciate the ability to extend these concepts to other conditions or fields of medicine. It should be noted that the surgical process is applicable to surgical procedures for brain, spine, knee and any other suitable region of the body.

Various apparatuses and processes will be described below to provide examples of implementations of the system disclosed herein. No implementation described below limits any claimed implementation and any claimed implementations may cover processes or apparatuses that differ from those described below. The claimed implementations are not limited to apparatuses or processes having all of the features of any one apparatus or process described below or to features common to multiple or all of the apparatuses or processes described below. It is possible that an apparatus or process described below is not an implementation of any claimed subject matter.

Furthermore, numerous specific details are set forth in order to provide a thorough understanding of the implementations described herein. However, it will be understood by those skilled in the relevant arts that the implementations described herein may be practiced without these specific details. In other instances, well-known methods, procedures and components have not been described in detail so as not to obscure the implementations described herein.

In this specification, elements may be described as "configured to" perform one or more functions or "configured for" such functions. In general, an element that is configured to perform or configured for performing a function is enabled to perform the function, or is suitable for performing the function, or is adapted to perform the function, or is operable to perform the function, or is otherwise capable of performing the function.

It is understood that for the purpose of this specification, language of "at least one of X, Y, and Z" and "one or more of X, Y and Z" may be construed as X only, Y only, Z only, or any combination of two or more items X, Y, and Z (e.g., XYZ, XY, YZ, ZZ, and the like) Similar logic may be applied for two or more items in any occurrence of "at least one . . . " and "one or more . . . " language.

Figure 1:
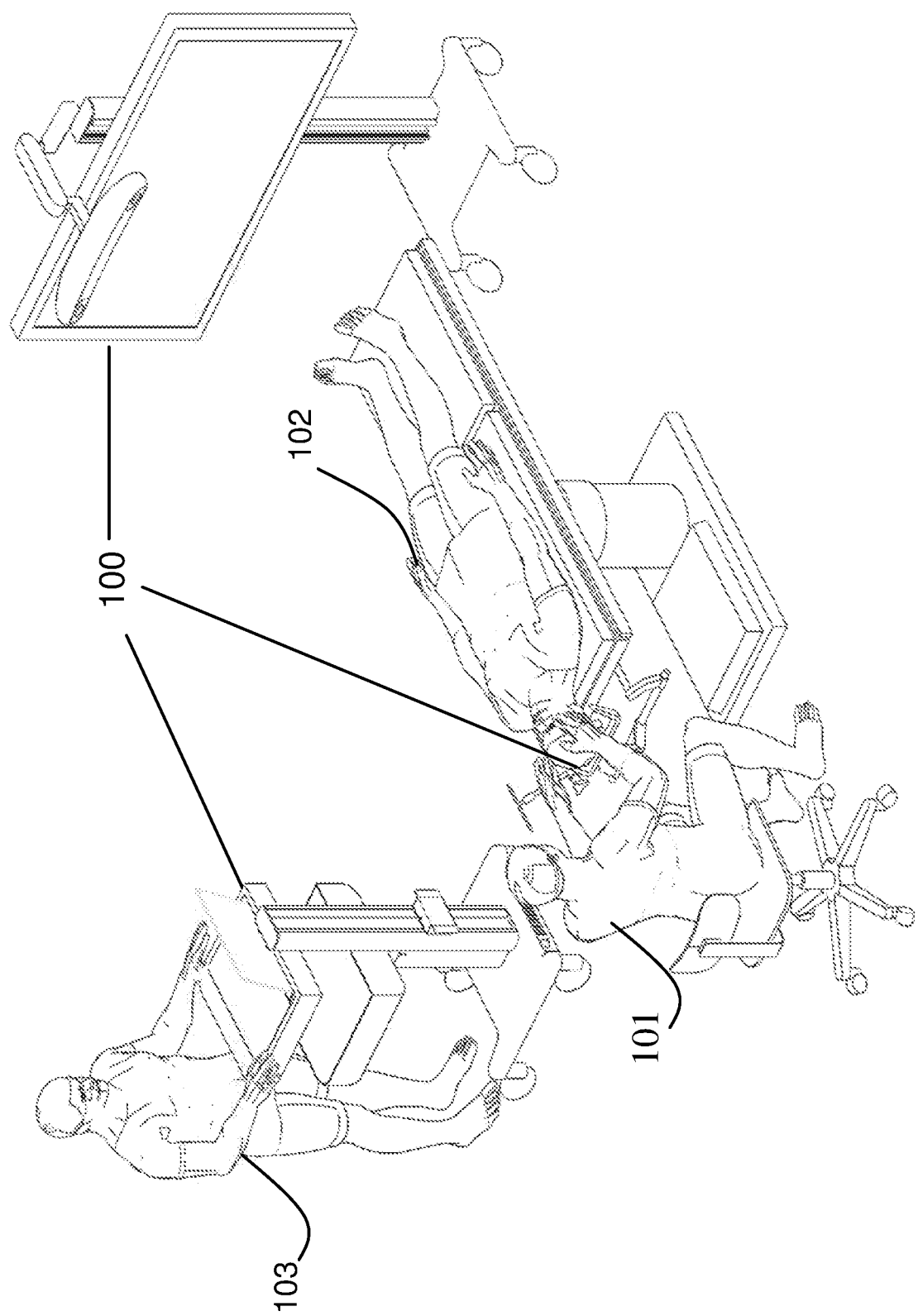
FIG. 1 shows an example operating room setup for a minimally invasive access port-based medical procedure, according to non-limiting implementations.

Referring to FIG. 1, a non-limiting example navigation system 100 is shown to support minimally invasive access port-based surgery. In FIG. 1, a neurosurgeon 101 conducts a minimally invasive port-based surgery on a patient 102 in an operating room (OR) environment. The navigation system 100 includes an equipment tower, tracking system, displays and tracked instruments to assist the surgeon 101 during the procedure. An operator 103 may also be present to operate, control and provide assistance for the navigation system 100.

Figure 2:
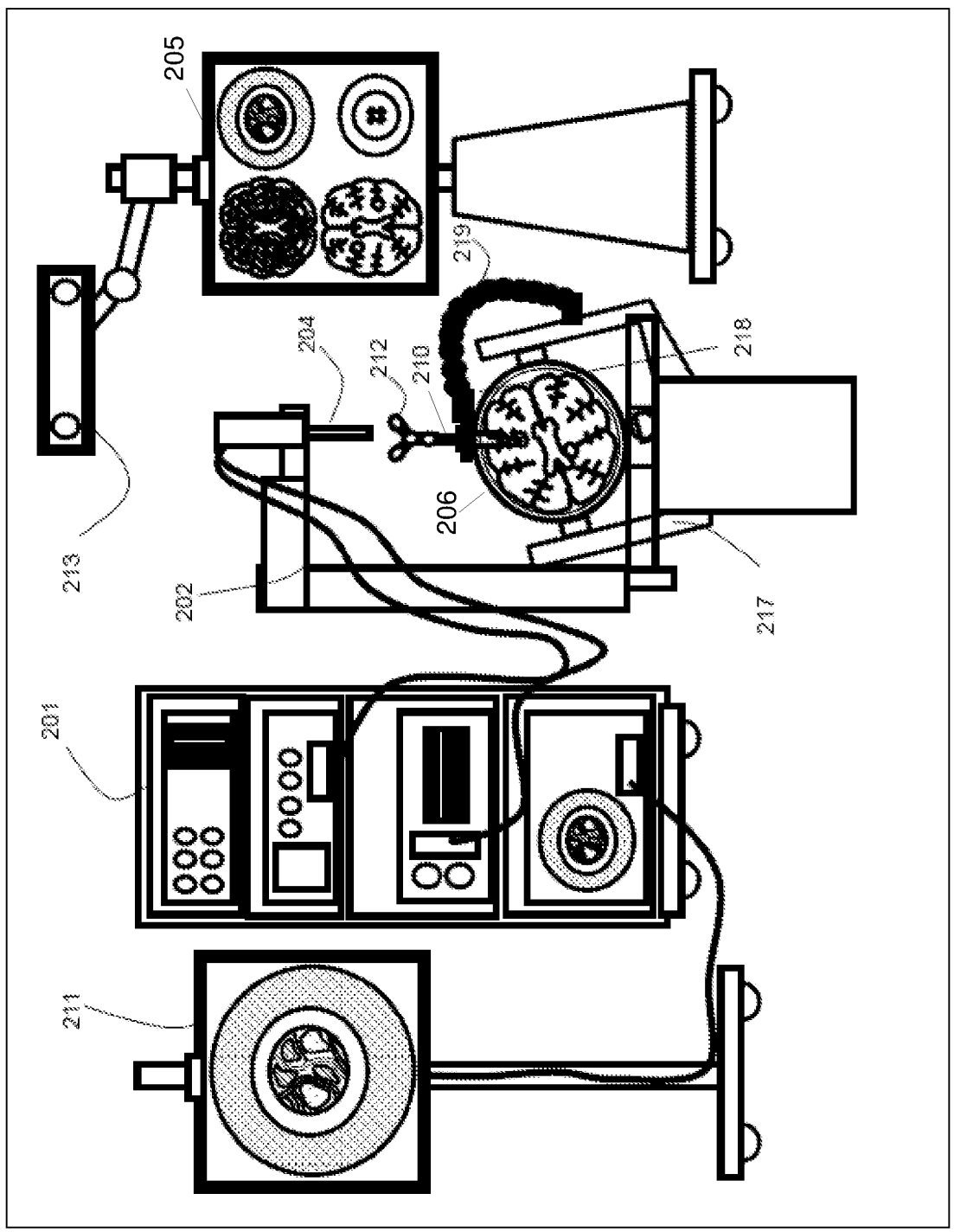
FIG. 2 is a block diagram illustrating components of a medical navigation system that may be used to implement a surgical plan for a minimally invasive surgical procedure, according to non-limiting implementations.

Referring to FIG. 2, a block diagram is shown illustrating components of an example medical navigation system 200, according to non-limiting implementations. The medical navigation system 200 illustrates a context in which a surgical plan including equipment (e.g., tool and material) tracking, such as that described herein, may be implemented. The medical navigation system 200 includes, but is not limited to, one or more monitors 205, 211 for displaying a video image, an equipment tower 201, and a mechanical arm 202, which supports an optical scope 204. The equipment tower 201 may be mounted on a frame (e.g., a rack or cart) and may contain a computer or controller (examples provided with reference to FIGS. 3 and 6 below), planning software, navigation software, a power supply and software to manage the mechanical arm 202, and tracked instruments. In one example non-limiting implementation, the equipment tower 201 may comprise a single tower configuration with dual display monitors 211, 205, however other configurations may also exist (e.g., dual tower, single display, etc.). Furthermore, the equipment tower 201 may also be configured with a universal power supply (UPS) to provide for emergency power, in addition to a regular AC adapter power supply.

A patient's anatomy may be held in place by a holder. For example, in a neurosurgical procedure the patient's head may be held in place by a head holder 217, and an access port 206 and an introducer 210 may be inserted into the patient's head. The introducer 210 may be tracked using a tracking camera 213, which provides position information for the navigation system 200. The tracking camera 213 may also be used to track tools and/or materials used in the surgery, as described in more detail below. In one example non-limiting implementation, the tracking camera 213 may comprise a 3D (three-dimensional) optical tracking stereo camera, similar to one made by Northern Digital Imaging (NDI), configured to locate reflective sphere tracking markers 212 in 3D space. In another example, the tracking camera 213 may comprise a magnetic camera, such as a field transmitter, where receiver coils are used to locate objects in 3D space, as is also known in the art. Location data of the mechanical arm 202 and access port 206 may be determined by the tracking camera 213 by detection of tracking markers 212 placed on these tools, for example the introducer 210 and associated pointing tools. Tracking markers may also be placed on surgical tools or materials to be tracked. The secondary display 205 may provide output of the tracking camera 213. In one example non-limiting implementation, the output may be shown in axial, sagittal and coronal views as part of a multi-view display.

As noted above with reference to FIG. 2, the introducer 210 may include tracking markers 212 for tracking. The tracking markers 212 may comprise reflective spheres in the case of an optical tracking system and/or pick-up coils in the case of an electromagnetic tracking system. The tracking markers 212 may be detected by the tracking camera 213 and their respective positions are inferred by the tracking software.

As shown in FIG. 2, a guide clamp 218 (or more generally a guide) for holding the access port 206 may be provided. The guide clamp 218 may optionally engage and disengage with the access port 206 without needing to remove the access port 206 from the patient. In some examples, the access port 206 may be moveable relative to the guide clamp 218, while in the guide clamp 218. For example, the access port 206 may be able to slide up and down (e.g., along the longitudinal axis of the access port 206) relative to the guide clamp 218 while the guide clamp 218 is in a closed position. A locking mechanism may be attached to or integrated with the guide clamp 218, and may optionally be actuatable with one hand, as described further below. Furthermore, an articulated arm 219 may be provided to hold the guide clamp 218. The articulated arm 219 may have up to six degrees of freedom to position the guide clamp 218. The articulated arm 219 may be lockable to fix its position and orientation, once a desired position is achieved. The articulated arm 219 may be attached or attachable to a point based on the patient head holder 217, or another suitable point (e.g., on another patient support, such as on the surgical bed), to ensure that when locked in place, the guide clamp 218 does not move relative to the patient's head.

Figure 3:
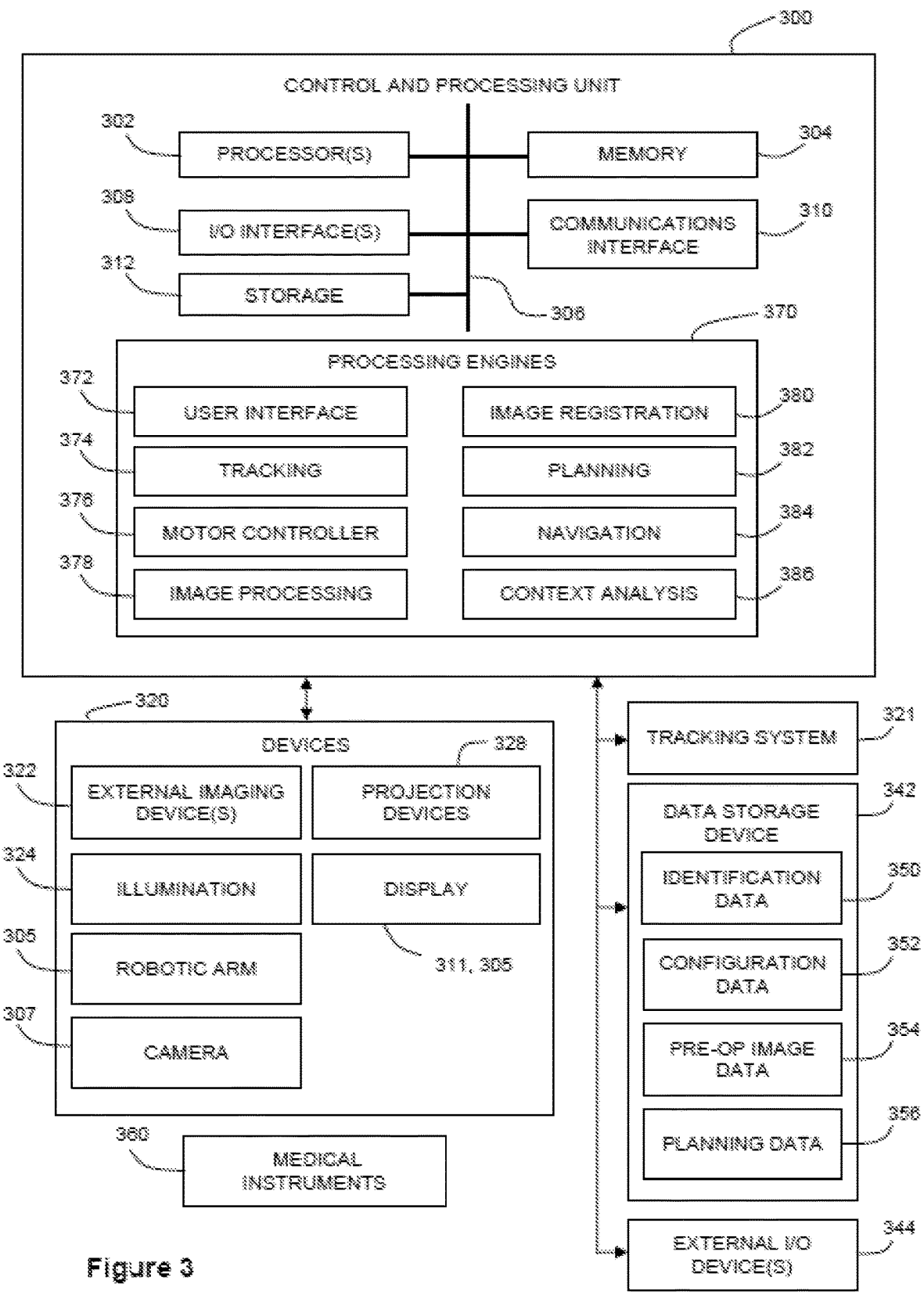
FIG. 3 depicts a block diagram illustrating components of a planning system used to plan a medical procedure that may then be implemented using the navigation system of FIG. 2, according to non-limiting implementations.

Referring to FIG. 3, a block diagram is shown illustrating a control and processing unit 300 that may be used in the navigation system 200 of FIG. 2 (e.g., as part of the equipment tower). In one example non-limiting implementation, control and processing unit 300 may include one or more processors 302, a memory 304, a system bus 306, one or more input/output interfaces 308, a communications interface 310, and storage device 312. In particular, one or more processors 302 may comprise one or more hardware processors and/or one or more microprocessors. Control and processing unit 300 may be interfaced with other external devices, such as tracking system 321, data storage device 342, and external user input and output devices 344, which may include, but is not limited to, one or more of a display, keyboard, mouse, foot pedal, and microphone and speaker. Data storage device 342 may comprise any suitable data storage device, including, but not limited to a local and/or remote computing device (e.g. a computer, hard drive, digital media device, and/or server) having a database stored thereon. In the example shown in FIG. 3, data storage device 342 includes, but is not limited to, identification data 350 for identifying one or more medical instruments 360 and configuration data 352 that associates customized configuration parameters with one or more medical instruments 360. Data storage device 342 may also include, but is not limited to, preoperative image data 354 and/or medical procedure planning data 356. Although data storage device 342 is shown as a single device in FIG. 3, in other implementations, data storage device 342 may be provided as multiple storage devices.

Medical instruments 360 may be identifiable using control and processing unit 300. Medical instruments 360 may be connected to and controlled by control and processing unit 300, and/or medical instruments 360 may be operated and/or otherwise employed independent of control and processing unit 300. Tracking system 321 may be employed to track one or more of medical instruments 360 and spatially register the one or more tracked medical instruments 360 to an intraoperative reference frame. In another example, a sheath may be placed over a medical instrument 360 and the sheath may be connected to and controlled by control and processing unit 300.

Control and processing unit 300 may also interface with a number of configurable devices, and may intraoperatively reconfigure one or more of such devices based on configuration parameters obtained from configuration data 352. Examples of devices 320, as shown in FIG. 3, include, but are not limited, one or more external imaging devices 322, one or more illumination devices 324, a robotic arm, one or more projection devices 328, and one or more displays 305, 311.

Aspects of the specification may be implemented via processor(s) 302 and/or memory 304. For example, the functionalities described herein may be partially implemented via hardware logic in processor 302 and partially using the instructions stored in memory 304, as one or more processing modules 370 and/or processing engines. Example processing modules include, but are not limited to, user interface engine 372, tracking module 374, motor controller 376, image processing engine 378, image registration engine 380, procedure planning engine 382, navigation engine 384, and context analysis module 386. While the example processing modules are shown separately in FIG. 3, in one example non-limiting implementation the processing modules 370 may be stored in the memory 304 and the processing modules may be collectively referred to as processing modules 370.

It is to be understood that the system is not intended to be limited to the components shown in FIG. 3. One or more components of the control and processing unit 300 may be provided as an external component or device. In one example non-limiting implementation, navigation engine 384 may be provided as an external navigation system that is integrated with control and processing unit 300.

Some implementations may be implemented using processor 302 without additional instructions stored in memory 304. Some implementations may be implemented using the instructions stored in memory 304 for execution by one or more general purpose microprocessors. Thus, the specification is not limited to a specific configuration of hardware and/or software.

While some implementations may be implemented in fully functioning computers and computer systems, various implementations are capable of being distributed as a computing product in a variety of forms and are capable of being applied regardless of the particular type of machine or computer readable media used to actually effect the distribution.

At least some aspects disclosed may be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache and/or a remote storage device.

A computer readable storage medium, and/or a non-transitory computer readable storage medium, may be used to store software and data which, when executed by a data processing system, causes the system to perform various methods. The executable software and data may be stored in various places including for example ROM, volatile RAM, non-volatile memory and/or cache. Portions of this software and/or data may be stored in any one of these storage devices.

Examples of computer-readable storage media include, but are not limited to, recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions may be embodied in digital and analog communication links for electrical, optical, acoustical and/or other forms of propagated signals, such as carrier waves, infrared signals, digital signals, and the like. The storage medium may comprise the internet cloud, storage media therein, and/or a computer readable storage medium and/or a non-transitory computer readable storage medium, including, but not limited to, a disc.

At least some of the methods described herein are capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB (Universal Serial Bus) keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

According to one aspect of the present application, one purpose of the navigation system 200, which may include control and processing unit 300, is to provide tools to a surgeon and/or a neurosurgeon that will lead to the most informed, least damaging neurosurgical operations. In addition to removal of brain tumors and intracranial hemorrhages (ICH), the navigation system 200 may also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, aspects of the present specification may be applied to other suitable medical procedures.

Figure 4:
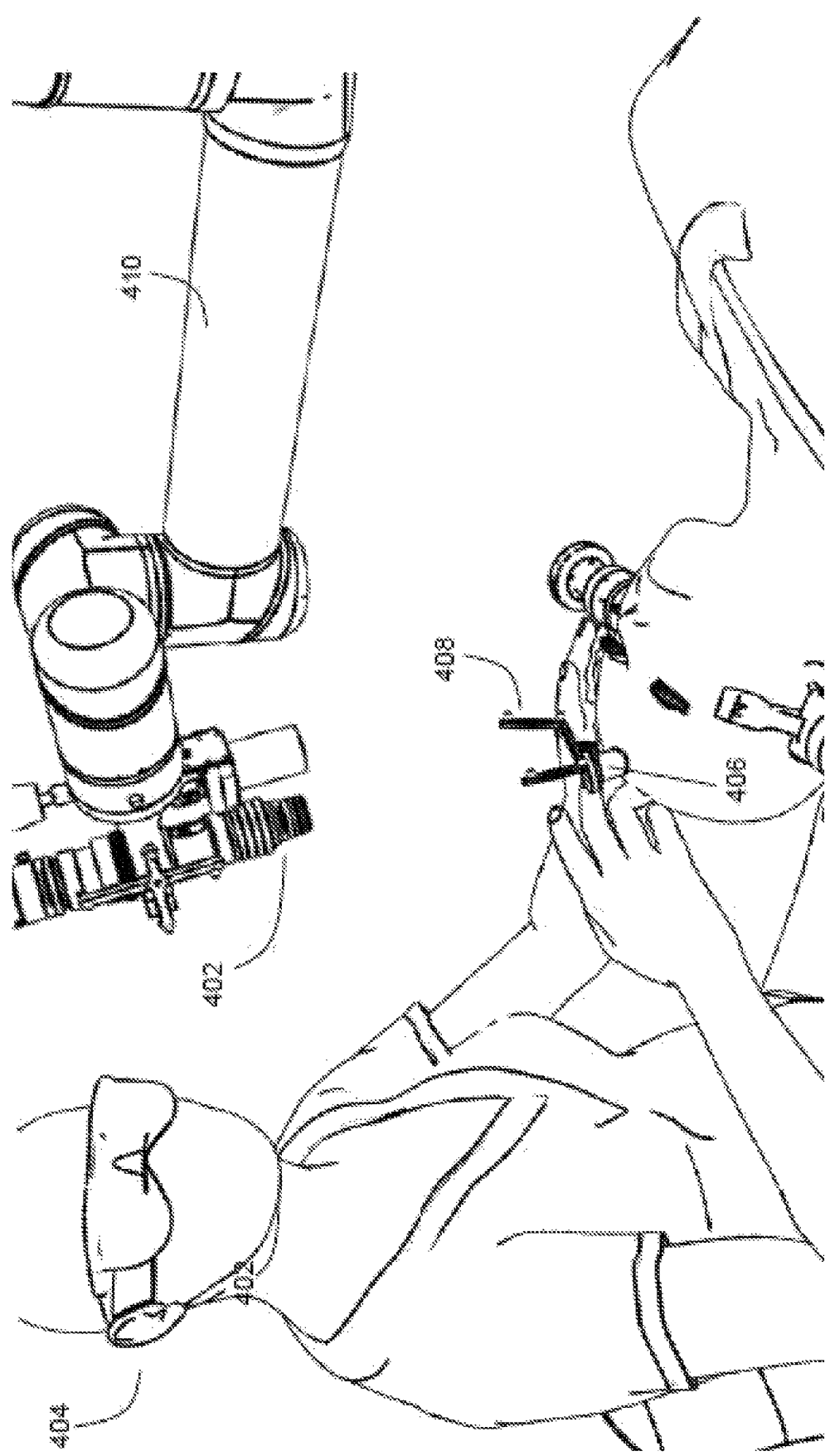
FIG. 4 depicts an example implementation port based brain surgery using a video scope, according to non-limiting implementations.

Attention is next directed to FIG. 4 which depicts a non-limiting example of a port-based brain surgery procedure using a video scope. In FIG. 4, operator 404, for example a surgeon, may align video scope 402 to peer down port 406. Video scope 402 may be attached to an adjustable mechanical arm 410. Port 406 may have a tracking tool 408 attached to it where tracking tool 408 is tracked by a tracking camera of a navigation system.

Even though the video scope 402 may comprise an endoscope and/or a microscope, these devices introduce optical and ergonomic limitations when the surgical procedure is conducted over a confined space and conducted over a prolonged period such as the case with minimally invasive brain surgery.

Figure 5:
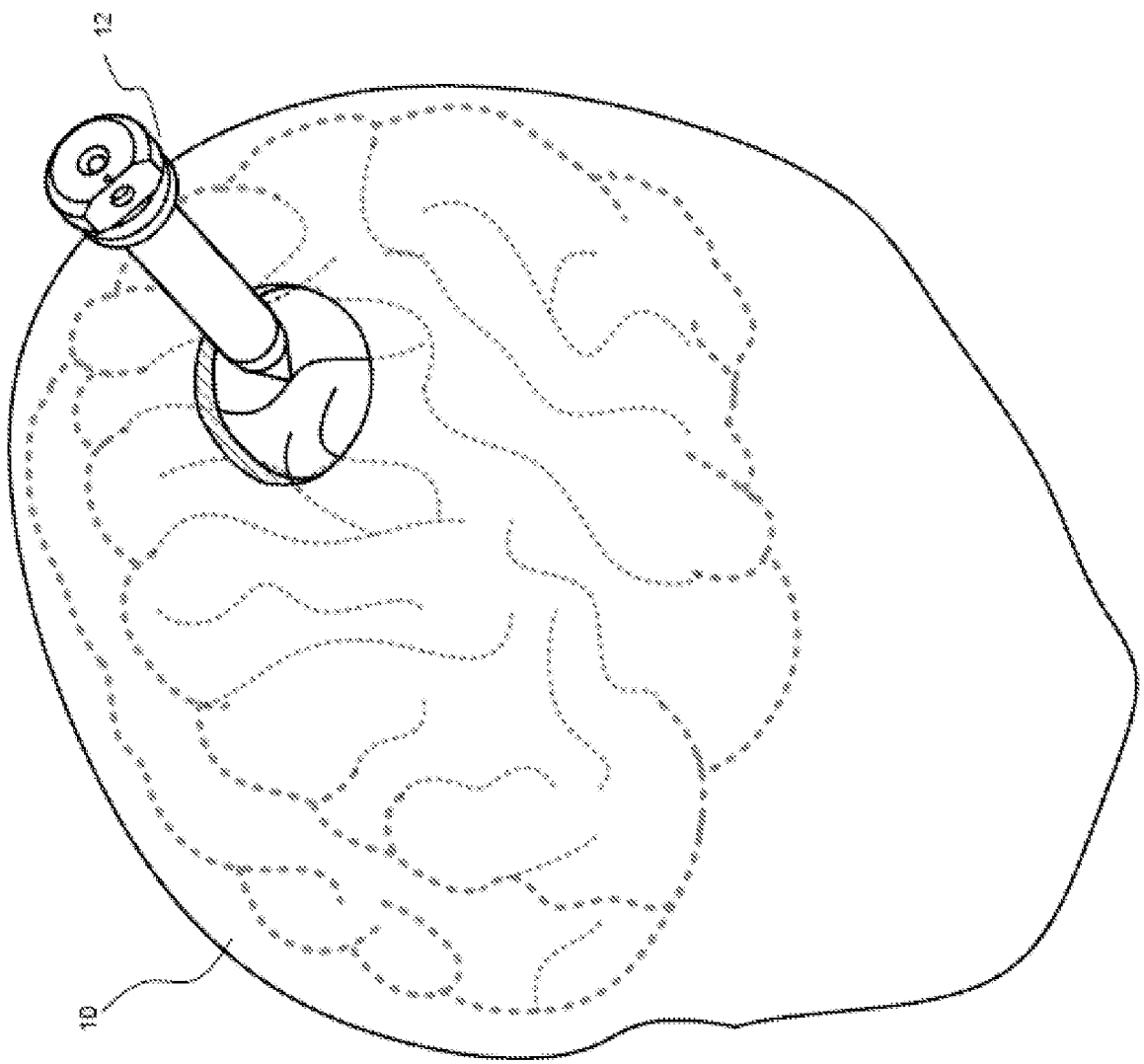
FIG. 5 depicts insertion of an access port into a human brain, for providing access to interior brain tissue during a medical procedure, according to non-limiting implementations.

FIG. 5 illustrates the insertion of an access port 12 into a human brain 10, in order to provide access to interior brain tissue during a medical procedure. In FIG. 5, access port 12 is inserted into a human brain 10, providing access to interior brain tissue. Access port 12 may include, but is not limited to, instruments such as catheters, surgical probes, and/or cylindrical ports such as the NICO BrainPath. Surgical tools and instruments may then be inserted within a lumen of the access port 12 in order to perform surgical, diagnostic or therapeutic procedures, such as resecting tumors as necessary. However, the present specification applies equally well to catheters, DBS needles, a biopsy procedure, and also to biopsies and/or catheters in other medical procedures performed on other parts of the body.

In the example of a port-based surgery, a straight and/or linear access port 12 is typically guided down a sulci path of the brain. Surgical instruments and/or surgical tools would then be inserted down the access port 12.

Figure 6:
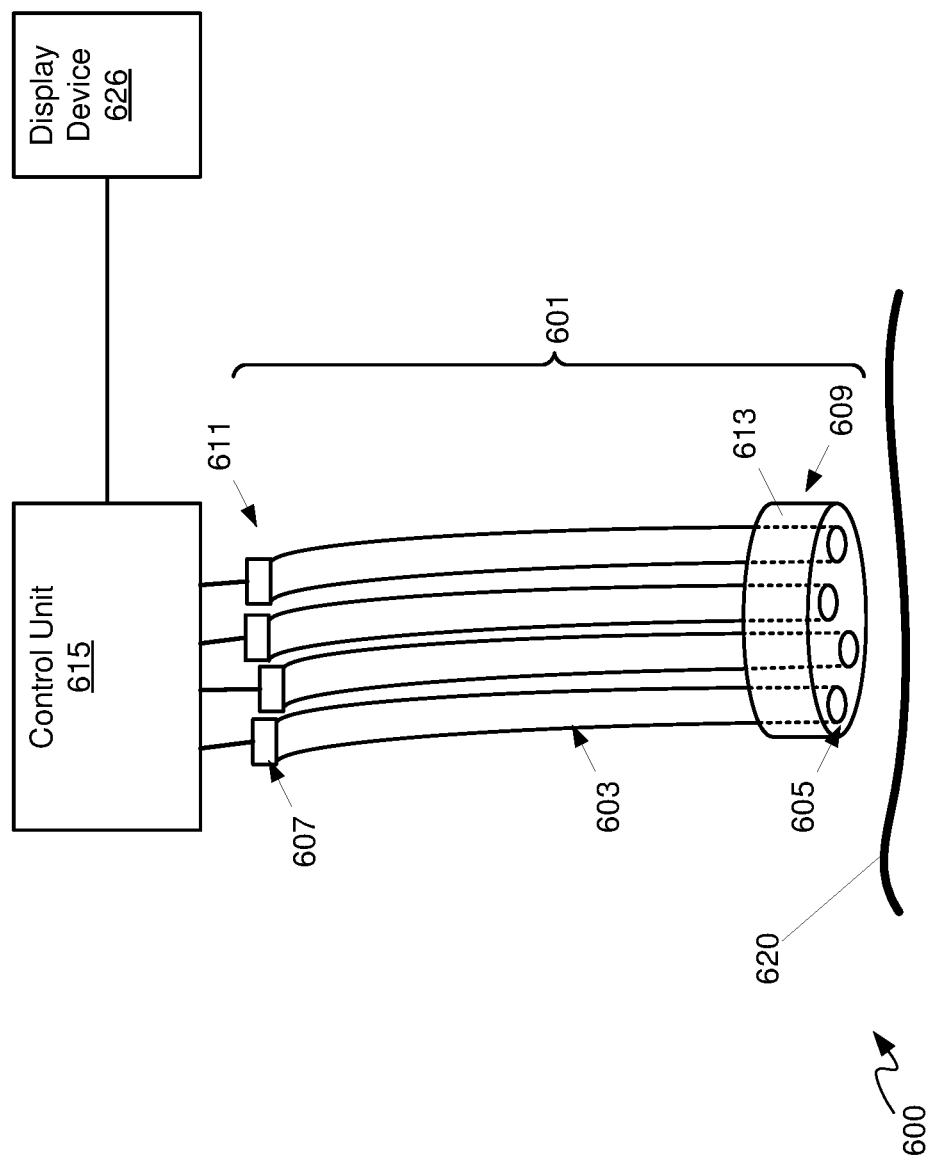
FIG. 6 depicts a schematic diagram of a system that includes a flexible high resolution endoscope, according to non-limiting implementations.

Attention is next directed to FIG. 6, which depicts a schematic diagram of a system 600 that includes an example of a flexible high resolution endoscope 601 that could be used with access port 12. It is appreciated that elements of system 600 are not drawn to scale, but are depicted schematically to show functionality. Endoscope 601 comprises: a plurality of optical fiber bundles 603; a plurality of lenses 605 in a one-to-one relationship with plurality of optical fiber bundles 603; and, a plurality of cameras 607 in a one-to-one relationship with the plurality of optical fiber bundles 603, each respective optical fiber bundle 603, of the plurality of optical fiber bundles 603, having a respective lens 605, of the plurality of lenses 605, located at a respective distal end 609, and a camera 607, of the plurality of cameras 607, located at a respective proximal end 611, plurality of optical fiber bundles 603 being coupled together at a common distal end 609, and otherwise being uncoupled from one another, a bending radius of endoscope 601 defined by a largest respective bending radius of each of the plurality of optical fiber bundles 603. As depicted, plurality of lenses 605 are each formed in a common optical element 613 located at common distal end 609, which also couples together plurality of optical fiber bundles 603 at common distal end 609. It is appreciated that respective distal ends 609 of each optical fibre bundle 603 are coincident with common distal end 609, such each of distal ends 609 and common distal end 609 are similarly numbered.

As depicted, system 600 further comprises a controller 615, coupled to each of cameras 607, and a display device 626, as described in more detail below.

In general, endoscope 601 is configured to acquire a plurality of images of a tissue sample 620, which can include, but is not limited to, a tissue sample accessible via access port 12. In particular, respective distal ends 609 of the plurality of optical fiber bundles 603, and respective lenses 605 located at respective distal ends 609, can be spaced apart from one another to provide different views of objects (such as tissue sample 620) in front of the respective distal ends 609. In some of these implementations endoscope 601 can thereby form a plenoptic camera.

While only one of each of plurality of optical fiber bundles 603, plurality of lenses 605, and plurality of cameras 607 is indicated in FIG. 6, as depicted, endoscope 601 comprises four optical fiber bundles 603, four respective lenses 605 and four respective cameras 607. However, endoscope 601 can comprise as few as two of each of optical fiber bundles 603, lenses 605 and cameras 607, and can comprise more than four of each of optical fiber bundles 603, lenses 605 and cameras 607. However, at a minimum, endoscope 601 comprises the plurality of optical fiber bundles comprises a first optical fiber bundle 603 and a second optical fiber bundle 603, each having the respective lens 605 located at the respective distal end 609, and the respective camera 607 located at the respective proximal end 611, which can thereby form a three-dimensional camera.

Each optical fiber bundle 603 can comprise an optical fiber having a respective diameter of are less than or equal to about 2 mm (however, optical fiber bundles 603 need not have all the same diameter). In particular, each optical fiber bundle 603 can have a diameter that can convey images from respective lenses 605 to respective cameras 607 with resolutions similar to cameras 607. For example, 2 mm optical fiber bundles can convey images of resolutions of about 18 kilopixels, and hence cameras 607 can produce digital images have resolutions of about 18 kilopixels.

Furthermore, as each optical fiber bundle 603 is free to bend independent from every other optical fiber bundle 603, other than at common distal end 609, the bending radius of endoscope 601 is determined and/or defined by the individual bending radii of each optical fiber bundle 603 rather than a total bending radii if optical fiber bundles 603 were coupled together along their entire length. Put another way, a bending radius of endoscope 601 is defined by a largest respective bending radius of each of the plurality of optical fiber bundles 603. As such, optical fiber bundles 603 of any suitable diameter are within the scope of present implementations; for example, a specified bending radius of endoscope 601 can be used to select individual optical fibers that will meet this specification, rather than selecting optical fibers that, when coupled together, will meet this specification.

In other words, as is understood from FIG. 6, plurality of optical fiber bundles 603 are coupled together at common distal end 609 (e.g. by way of common optical element 613), and are otherwise uncoupled from one another. Indeed, each of plurality of optical fiber bundles 603 can bend from common distal end 609 independent of the other optical fiber bundles 603. As such plurality of optical fiber bundles 603 are not attached to each other than at common distal end 609.

Furthermore, each optical fiber bundle 603 can have a length that is commensurate with insertion through an access port (including, but not limited to, access port 12), as well as port-based surgery, such that common distal end 609 can be inserted through an access port, and optical fiber bundles 603 join respective lenses 605 to respective cameras 607 such that cameras 607 do not block surgical access to access port 12 (e.g. cameras 607 do not block access of a surgeon (and the like) and/or surgical tools (and the like) to access port 12). For example each optical fiber bundle 603 can be greater than about a half meter long. Furthermore, optical fiber bundles 603 need not all be the same length, and some optical fiber bundles 603 can be longer or shorter than other optical fiber bundles 603.

As depicted, each lens 605 is formed in common optical element 613 located at common distal end 609. Common optical element 613 can comprise one or more of optical glass and optical plastic, at least at a tissue facing side of common optical element 613. Each lens 605 can be formed in common optical element 613 using, for example, laser processing (including, but not limited to, femtosecond laser processing, and the like) to form profiles in the index of refraction in the glass and/or plastic of common optical element 613 which correspond to each lens 605. However, lenses 605 can also be tiled together using one or more of a mechanical assembly, adhesives, and the like.

Two or more of plurality of lenses 605 can have one or more of: different depths of field, different fields of view of objects in front of the plurality of lenses 605: and different angular view of objects in front of the plurality of lenses 605. Hence, when endoscope 601 is imaging tissue sample 620, tissue sample 620 can be imaged using at least two different depths of field and/or at least two different fields of view and/or at least two different angular views.

Each camera 607 can include, but is not limited to one or more of a charge-coupled device (CCD) camera, a digital camera, an optical camera, and the like, and is generally configured to acquire digital images, and in particular digital images received from a respective lens 605 via a respective optical fiber bundle 603. While not depicted, each camera 607 can further include one or more respective lenses for focusing light from a respective optical fiber 603 onto a respective imaging element (such as a CCD). While not depicted, endoscope 601 can include one or more devices for coupling optical fiber bundles 603 to a respective camera 607. Furthermore, each camera 607 can have a resolution of about 18 kilopixels.

Controller 615 can comprise any suitable combination of computing devices, processors, memory devices and the like. In particular, controller 615 can comprise one or more of a data acquisition unit, configured to acquire data and/or images at least from cameras 607, and an image processing unit, configured to process data and/or images from cameras 607 for rendering at display device 626. Hence, controller 615 is interconnected with cameras 607 and display device 626. In some implementations, controller 615 can comprise control and processing unit 300 depicted in FIG. 3, and/or controller 615 can be in communication with control and processing unit 300 depicted in FIG. 3 and/or controller 615 can be under control of communication with control and processing unit 300 depicted in FIG. 3.

In some implementations, however, controller 615 can be a component of endoscope 601 such that endoscope 601 comprises controller 615. In these implementations, endoscope 601 can be provided as a unit with controller 615 which can be interfaced with control and processing unit 300 depicted in FIG. 3, and the like.

Display device 626 can comprise any suitable display device including, but not limited to, cathode ray tubes, flat panel displays, and the like. For example, display device 626 can comprise one or more of monitors 205, 211, as depicted in FIG. 2, and/or displays 305, 311 depicted in FIG. 3.

Figure 7:
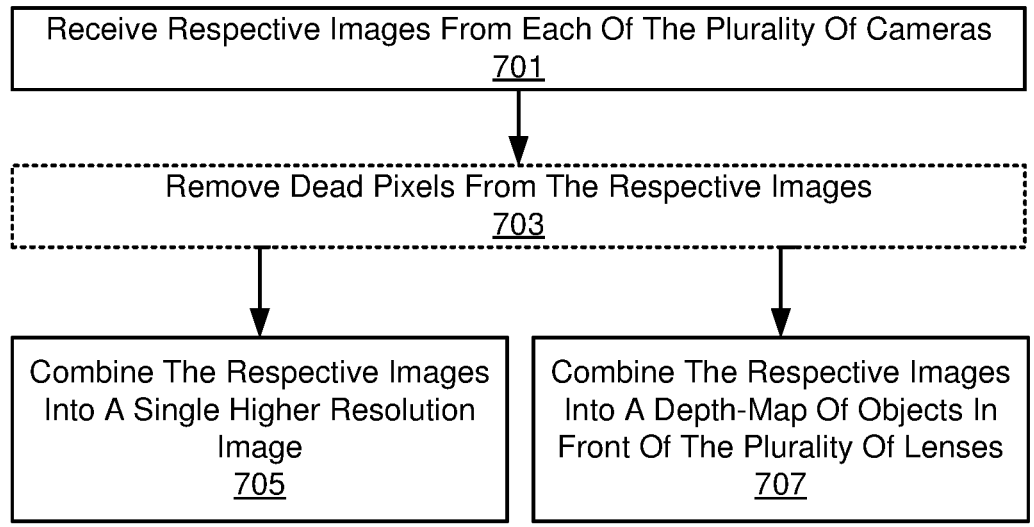
FIG. 7 depicts a block diagram of a flowchart of a method for combining images using, for example, the flexible high resolution endoscope of FIG. 6, according to non-limiting implementations.

Attention is now directed to FIG. 7 which depicts a flowchart of a method 700 for combining images from cameras, according to non-limiting implementations. In order to assist in the explanation of method 700, it will be assumed that method 700 is performed using system 600, and specifically by controller 615. Indeed, method 700 is one way in which system 600 and/or controller 615 can be configured. Furthermore, the following discussion of method 700 will lead to a further understanding of controller 615, and system 600 and its various components. However, it is to be understood that system 600 and/or controller 615 and/or method 700 can be varied, and need not work exactly as discussed herein in conjunction with each other, and that such variations are within the scope of present implementations.

Regardless, it is to be emphasized, that method 700 need not be performed in the exact sequence as shown, unless otherwise indicated; and likewise various blocks may be performed in parallel rather than in sequence; hence the elements of method 700 are referred to herein as "blocks" rather than "steps". It is also to be understood, however, that method 700 can be implemented on variations of system 600 as well.

At block 701, controller 615 receives respective images from each of plurality of cameras 607.

At an optional block 703 (indicated by block 703 being shown in broken lines), controller 615 removes dead pixels from the respective images. In some implementations, block 703 is not performed. Furthermore, in other implementations, when no dead pixels are in the respective images, block 703 is not performed.

At block 705, controller 615 can combine the respective images into a single higher resolution image.

At block 707, controller 615 can combine the respective images into a depth-map of objects in front of the plurality of lenses 605 using, for example, light field processing techniques, and the like.

In some implementations, controller 615 can implement both blocks 705, 707, for example in parallel with each other and/or one after the other. In other implementations, controller 615 can implement one of blocks 705, 707.

Furthermore, in some implementations, controller 615 can implement blocks 703 in conjunction with one or more of blocks 705, 707.

Method 700 will now be described with respect to FIG. 8, which is substantially similar to FIG. 6, with like elements having like numbers, however in FIG. 8, respective distal ends 609 and respective proximal ends 611 are enlarged, and the entire length of each optical fiber bundle 603 is not depicted.

Figure 8:
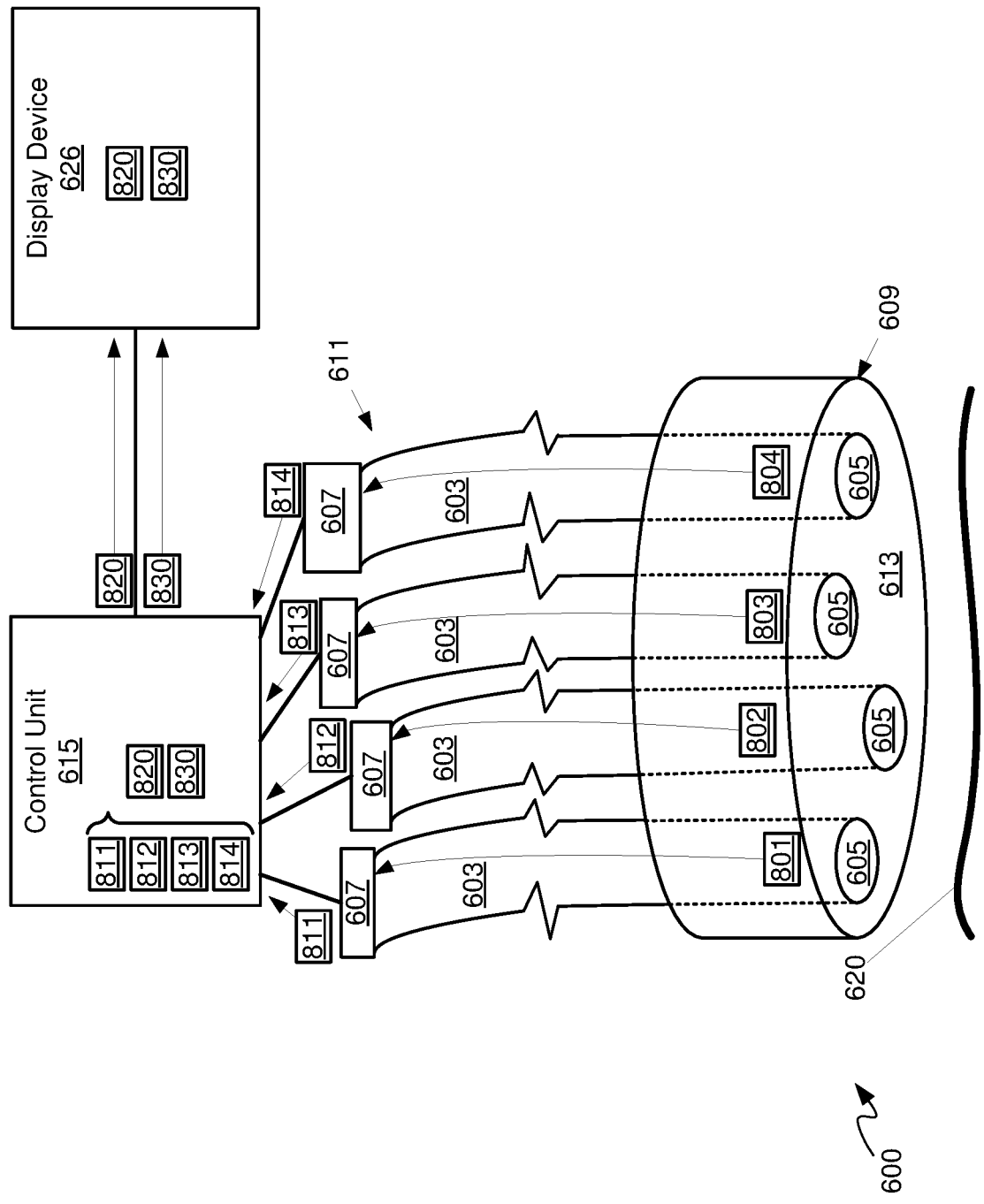
FIG. 8 depicts the system of FIG. 6 in use, according to non-limiting implementations.

In FIG. 8, light 801, 802, 803, 804 representing different respective views of tissue sample 620 is collected by respective lenses 601 and conveyed to respective cameras 607 by respective optical fiber bundles 603. Cameras 607 convert light 801, 802, 803, 804 into respective digital images 811, 812, 813, 814 of tissue sample 620, which are received at controller 615 (e.g. at block 701 of method 700).

Controller 615 processes digital images 811, 812, 813, 814 to optionally remove dead pixels in each of digital images 811, 812, 813, 814 (e.g. at block 703 of method 700), and combine digital images 811, 812, 813, 814 image into one or more of single higher resolution image 820 of tissue sample 620 (e.g. at block 705 of method 700), and a depth-map 830 of tissue sample 620 (e.g. at block 707 of method 700). Controller 615 can be configured to produce higher resolution image 820 and/or depth-map 830 from digital images 811, 812, 813, 814 using light field processing, as known to persons of skill in the art. Controller 615 can then provide higher resolution image 820 and/or depth-map 830 to display device 626 for rendering thereupon. Controller can optionally provide one or more of digital images 811, 812, 813, 814 to display device 626 for rendering thereupon (not depicted).

In other words, dead pixels of digital images 811, 812, 813, 814 and pixels of digital images 811, 812, 813, 814 can be combined and/or interlaced and/or used to produce interpolated pixels to produce image 820 which has a higher resolution of each of digital images 811, 812, 813, 814 taken alone. Hence, if each of digital images 811, 812, 813, 814 has a resolution of about 18 kilopixels, image 820 can have a resolution can at least about double 18 kilopixels. Thus, endoscope 601 can be configured to images having resolutions similar to those produced by existing high resolution endoscopes, but without the attendant problems with bending radius suffered by those existing high resolution endoscopes.

In addition, using light field processing of the separate digital images 811, 812, 813, 814 from cameras 607, a depth-map of tissue sample 620 (or any other object) imaged by lenses 605 can be reconstructed, which can allow structures with differing depth to be more easily detected and/or see.

Furthermore, when endoscope 601 is configured for omnifocusing (having all objects imaged by lenses 605 in focus), selective post-acquisition focusing, and depth of field control can be possible, both in post-acquisition and real-time. This post-processing can also allow for removal of dead pixels which can be caused by broken fibres within fiber bundles without significant loss of detail. In other words, block 703 can be performed in conjunction with either of blocks 705, 707.

Furthermore, in some implementations, two or more of digital images 811, 812, 813, 814 can be combined into a stereo image of tissue sample 620. Indeed, a plurality of pairs of digital images 811, 812, 813, 814 can be combined to produce a plurality of stereo images of tissue sample 620, for example from different angles and/or different fields of view and/or different depths of field.

In yet further implementations, where lenses 605 have different depths of field, but a similar field of view, digital images 811, 812, 813, 814 can be combined into a plenoptic image of tissue sample 620 such that a depth of field of the plenoptic image can be selected by a user interacting with controller 615, display device 626 and an input device (not depicted).

Indeed, in these implementations, lenses 605 can be configured for omnifocusing, where all objects (e.g. including, but not limited to tissue sample 620) imaged by lenses 605 are in focus; while each individual lens 605 may not have all objects in focus, collectively lenses 605 can image all objects in focus such that, collectively, all images produced by cameras 607 include all objects imaged by lenses 605 in focus, at least in one of the images.

Figure 9:
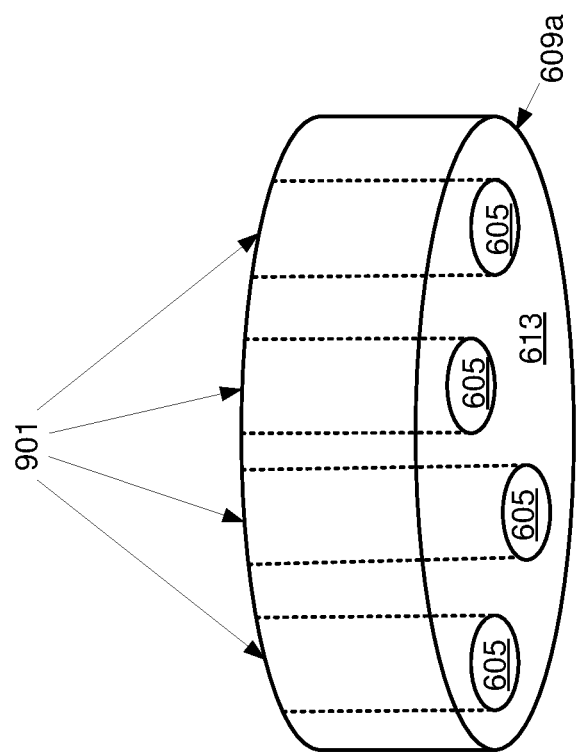
FIG. 9 depicts an optical element of the flexible high resolution endoscope of FIG. 6, according to non-limiting implementations.

Attention is next directed to FIG. 9 which depicts common optical element 613. Common optical element 613 is generally configured to both provide lenses 605 and couple together the plurality of optical fiber bundles 603 at common distal end 609.

Hence, common optical element 613 comprises lenses 605 and, as depicted, respective slots 901 for receiving a respective optical fiber bundle 603 on a proximal side, each slot 901 in a body of common optical element 613, and each slot 901 terminating at a respective lens 605 at distal end 609.

Hence, each slot 901 has a diameter that is similar to a diameter of a respective optical fiber bundle 603 such that each slot 901 can receive a respective optical fiber bundle 603 and seat a distal end of each respective optical fiber bundle 603 at a respective lens 605.

While not depicted, common optical element 613 can further comprise a mechanism for fixing each respective optical fiber bundle 603 within a respective slot 901; alternatively, adhesives (including, but not limited to optical adhesives) can be used to fix a respective optical fiber bundle 603 within a respective slot 901.

Figure 10:
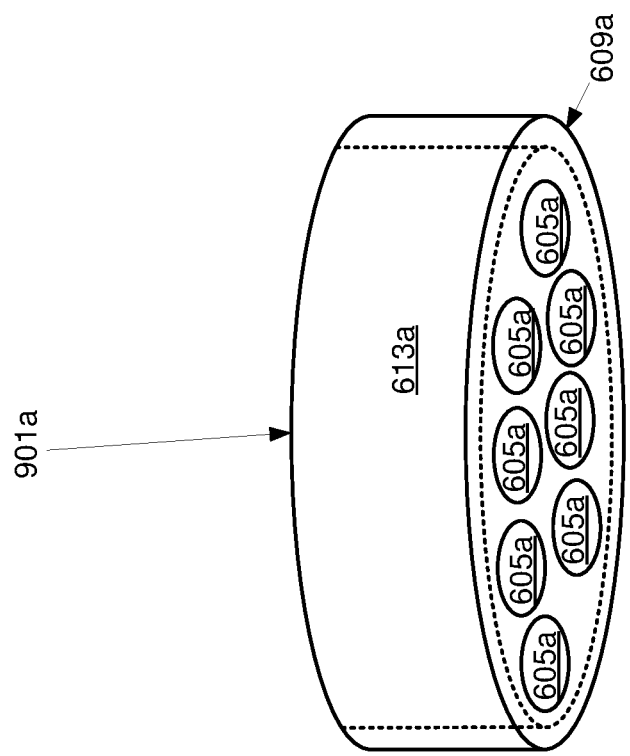
FIG. 10 depicts an alternative optical element that can be used with the flexible high resolution endoscope of FIG. 6, according to non-limiting implementations.

Attention is next directed to FIG. 10 which depicts an alternative common optical element 613a, which is substantially similar to optical element 613, with like elements having like numbers, however with an "a" appended thereto. Hence, optical element 613a comprises a plurality of lenses 605a at a distal end 609a. However, in contrast to optical element 613, optical element 613a comprises eight lenses 605a, and one slot 901a configured to receive a plurality of optical fiber bundles. However, optical element 613a can comprise fewer than eight lenses 605a and more than eight lenses 605a.

Figure 11:
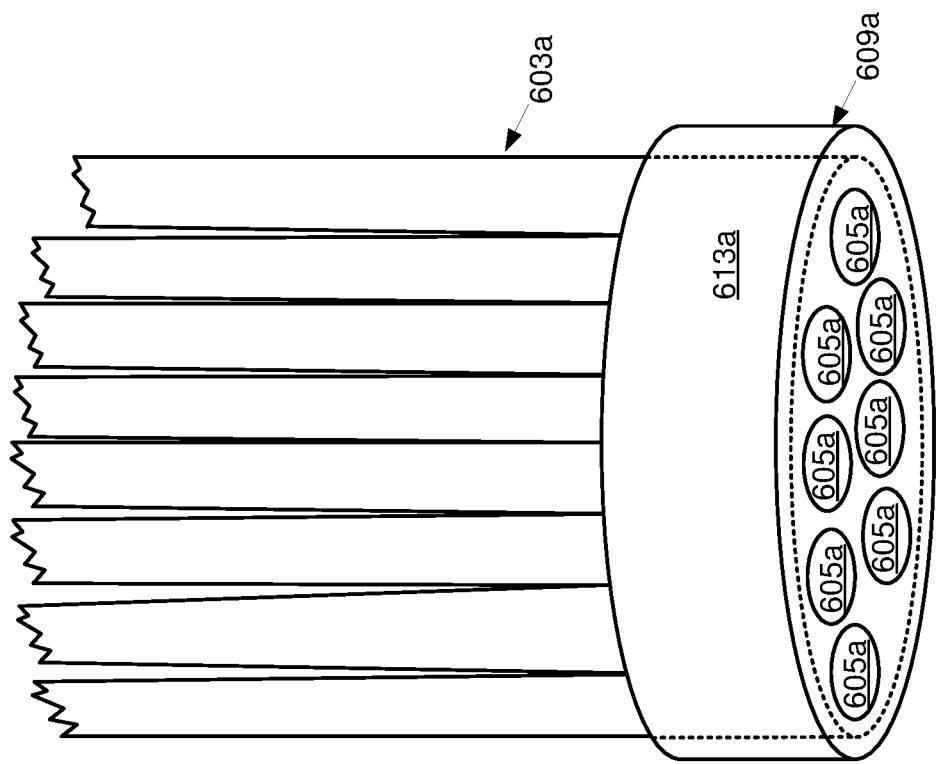
FIG. 11 depicts the optical element of FIG. 10 in an alternative use scenario, according to non-limiting implementations.

Attention is next directed to FIG. 11 which depicts slot 901a of optical element 613a receiving a plurality of optical fiber bundles 603a, in a one-to-one relationship with plurality of lenses 605a, optical fiber bundles 603a being coupled together a common distal end 609a, and otherwise being uncoupled from one another. While only a portion of optical fiber bundles 603a is depicted, it is assumed that each optical fiber bundle 603a is coupled to a respective camera at a proximal end, similar to implementations depicted in FIG. 6.

In particular, coupling together of optical fiber bundles 603a at common distal end 609a results in a total diameter of coupled optical fiber bundles 603a that is about a same diameter as slot 901a. While not depicted, distal ends of optical fiber bundles 603a are aligned with a respective lens 605a, as in system 600. For example, a geometry of distal ends of optical fiber bundles 603a can be selected so that when distal ends of optical fiber bundles 603a are coupled together, they form a geometric pattern, and lenses 605a can be arranged into a similar pattern. Hence, when distal ends of optical fiber bundles 603a are inserted into slot 901a, one or more of distal ends of optical fiber bundles 603a and common optical element 613a can be rotated until alignment with lenses 605a occurs. Such alignment can be determined by one or more of processing and viewing images from cameras to which each optical fiber bundle 603a is coupled.

Alternatively, distal ends of optical fiber bundles 603a can have a cross-section of a given geometric shape, for example a geometric shape having at least one flat side, and a respective cross-section slot 901a can have a similar shape; hence, when distal ends of optical fiber bundles 603a are inserted into slot 901a the flat sides align which can cause the distal ends of optical fiber bundles 603a to align with lenses 605a.

Alternatively, a mechanical assembly can be used to couple together distal ends of optical fiber bundles 603a and further space distal ends of optical fiber bundles 603a in a pattern similar to lenses 605a; in these implementations, slot 901a can be adapted to receive the distal ends of optical fiber bundles 603a and the mechanical assembly.

Figure 12:
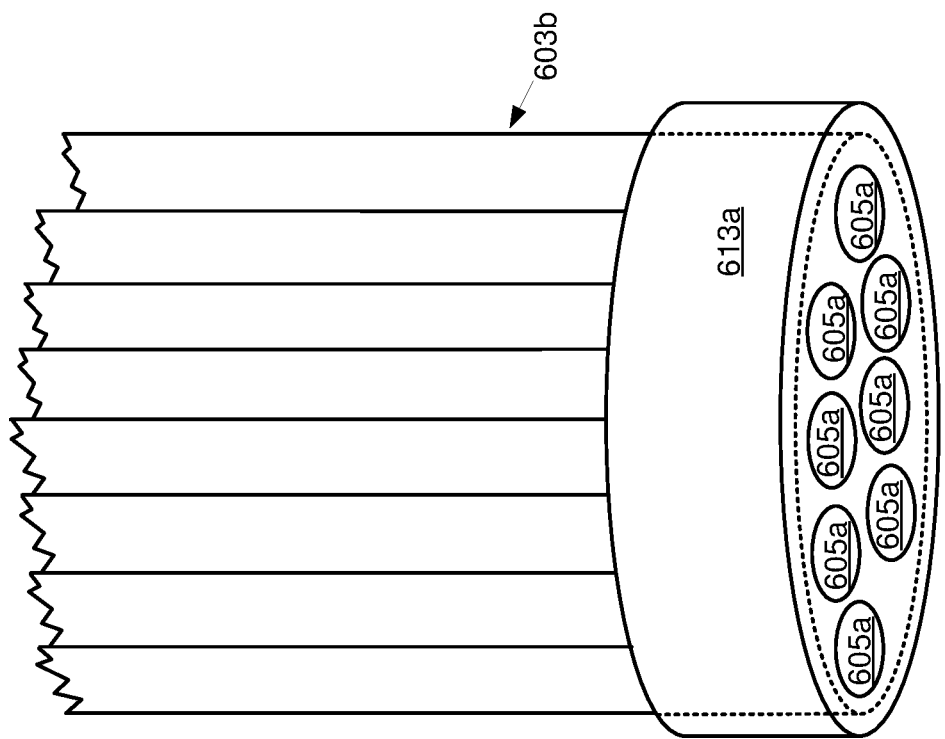
FIG. 12 depicts the optical element of FIG. 10 in a further alternative use scenario, according to non-limiting implementations.

Attention is next directed to FIG. 12 which depicts common optical element 613a being used with an optical fiber bundle 603b having a similar diameter to that of slot 901a, and can include a plurality of optical fiber bundles coupled together at common distal end 609a, as well as along their length. Hence, optical fiber bundle 603b is configured to convey images from lenses 605a to one or more cameras at a common proximal end. Indeed, individual optical fiber bundles of optical fiber bundle 603b need not be aligned with lenses 605a as a proximal end of optical fiber bundle 603b can have a diameter that can receive light from all of lenses 605a. The bending radius of optical fiber bundle 603b is larger than a bending radius of endoscope 601, however such difference in bending radius does not preclude use of common optical element 613a with more typical endoscopes.

Figure 13:
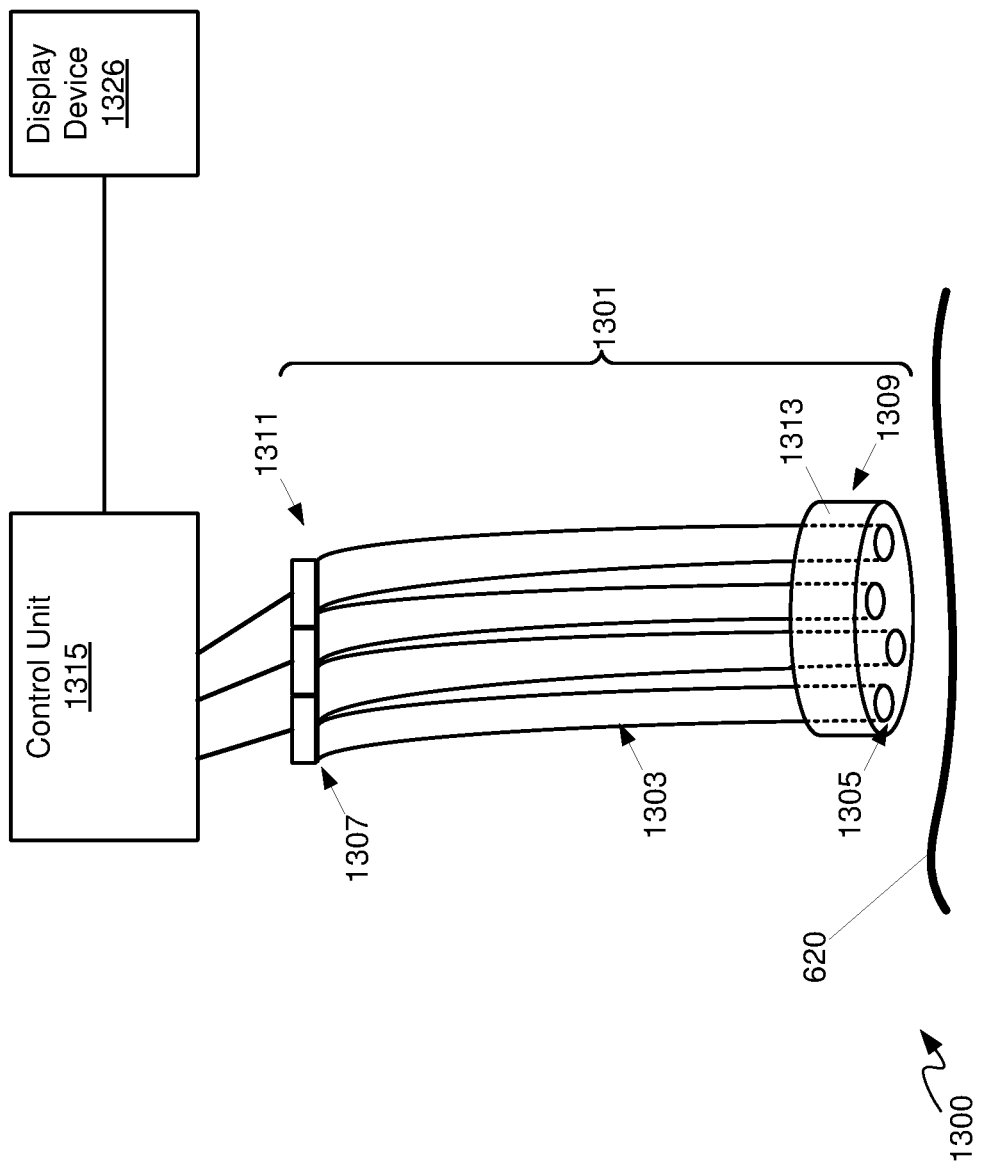
FIG. 13 depicts a schematic diagram of a system that includes an alternative flexible high resolution endoscope, according to non-limiting implementations.

Attention is next directed to FIG. 13, which depicts an alternative system 1300 that includes an example of a flexible high resolution endoscope 1301 that could be used with access port 12 to image tissue sample 620. System 1300 is substantially similar to system 600, with like elements having like numbers, but in a "1300" series rather than a "600" series. However, in contrast to endoscope 601, optical fiber bundles of endoscope 1301 are coupled together at both a common distal end and a common proximal end, and are otherwise uncoupled, and cameras used with endoscope 1301 are not necessarily in a one-to-one relationship with the optical fiber bundles.

Hence, endoscope 1301 comprises: a plurality of optical fiber bundles 1303; a plurality of lenses 1305 in a one-to-one relationship with plurality of optical fiber bundles 1303; and, one or more cameras 1307. Each respective optical fiber bundle 1303, of the plurality of optical fiber bundles 1303, has a respective lens 1305, of the plurality of lenses 1305, located at a respective distal end 1309. One or more cameras 1307 are located at a common proximal end 1311 of the plurality of optical fiber bundles 1303. Plurality of optical fiber bundles 1303 are coupled together at a common distal end 1309 and at common proximal end 1311, and are otherwise uncoupled from one another. As depicted, plurality of lenses 1305 are each formed in a common optical element 1313 similar to common optical element 613. As depicted, system 1300 further comprises a controller 1315, coupled to each of one or more cameras 1307, and a display device 1326.

While endoscope 1301, as depicted, includes three cameras 1307, in other implementations endoscope 1301 could include as few as one camera 1307 and more than three cameras 1307, including more than four cameras 1307. It is assumed, however that cameras 1307 of endoscope 1301 are collectively configured to receive light from all of optical fiber bundles 1303, and that each of one or more cameras 1307 can be arranged to receive images from one or more of plurality of optical fiber bundles 1303

Hence, in these implementations, respective alignment of distal and proximal ends of optical fiber bundles 1303 with lenses 1305 and one or more cameras 1307 is less important than in system 600, as each of one or more cameras 1307 can be arranged to receive images from one or more of plurality of optical fiber bundles 1303. Controller 1315 can hence be configured to separate and/or combine images from each of one or more cameras 1307 into images corresponding to fields of view of each of lenses 1305.

Indeed while, as depicted, each of distal ends of plurality of optical fiber bundles 1303 is aligned with a respective lens 1305, in other implementations, more than one of plurality of optical fiber bundles 1303 can be arranged to receive light from one or more of lenses 1305, such that plurality of optical fiber bundles 1303 functions optically as a larger optical fiber bundle similar to that depicted in FIG. 12. Indeed, in some implementations, common optical element 1313 can be replaced with common optical element 613*a* having one larger slot 901*a* instead of individual slots.

However, as each of plurality of optical fiber bundles 1303 are free to bend individually, other than at ends 1309, 1311, a bending radius of endoscope 1301 is determined by the bending radii of individual optical fiber bundles 1303 rather than all of optical fiber bundles 1303 bending together.

Hence, provided herein is a flexible endoscope that comprises of multiple optical fibre bundles which can each have about 18 kilopixels resolution, each coupled to a multi-lens array at a distal end and multiple cameras at a proximal end. Each lens on the array can convey a separate image to the distal end of each optical fibre bundle and cameras coupled to the proximal end of the optical fibre bundles acquire separate pixelated images. These lower resolution images, acquired by each of the cameras, can merged and/or combined, and reconstructed using principles of light field imaging and processing, to produce a super-resolution image This can allow for much higher resolution imaging than with conventional endoscopes, which can allow for better diagnosis and treatment.

Furthermore, using light field processing of the separate images from the cameras, a depth-map of objects imaged by the lenses can be reconstructed, which can allow structures with differing depth to be more easily detected and/or seen. By taking advantage of the underlying optics of the method, omnifocusing (having all object in the scene in-focus), selective post-acquisition focusing, and depth of field control is possible post-acquisition and real-time. This post-processing can allow for removal of "dead" pixels which can be caused by broken fibres within fiber bundles without significant loss of detail Using separate fibre bundles can also resolve flexibility issues associated with having one large fibre bundle, since each smaller fiber bundle can move independently from one another and not seize when bent.

While devices and methods described herein have been described with respect to surgical and/or medical applications, devices and methods described herein can be used other fields, such as in engineering and defense, in in particular in scenarios where high-resolution three-dimensional imaging of a space and/or objects occurs through a small, (and even convoluted) access port.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. An endoscope comprising:
   a plurality of optical fiber bundles;
   a plurality of lenses in a one-to-one relationship with the plurality of optical fiber bundles;
   a plurality of cameras in a one-to-one relationship with the plurality of optical fiber bundles,
   each respective optical fiber bundle, of the plurality of optical fiber bundles, having a respective lens, of the plurality of lenses, located at a respective distal end, and a camera, of the plurality of cameras, located at a respective proximal end,
   the plurality of optical fiber bundles being coupled together at a common distal end, and otherwise being uncoupled from one another, a bending radius of the endoscope defined by a largest respective bending radius of each of the plurality of optical fiber bundles; and
   a common optical element, wherein the plurality of lenses are each formed in the common optical element, the common optical element located at the common distal end, the common optical element being one or more of: removable from the common distal end of the plurality of optical fiber bundles; and disposable,
   wherein one lens of the plurality of lenses comprises a distinct depth of field and a distinct angle of view in relation to another lens of the of the plurality of lenses.

2. The endoscope of claim 1, wherein the plurality of optical fiber bundles comprises a first optical fiber bundle and a second optical fiber bundle, each optical fiber bundle having the respective lens located at the respective distal end, and the respective camera located at the respective proximal end, thereby forming a three-dimensional camera.

3. The endoscope of claim 1, wherein respective distal ends of the plurality of optical fiber bundles and respective lenses located at the respective distal ends are spaced apart from one another to provide a plurality of distinct views of objects in front of the respective distal ends.

4. The endoscope of claim 1, wherein the one lens of the plurality of lenses further comprises a distinct field of view in relation to the other lens of the of the plurality of lenses.

5. The endoscope of claim 1, further comprising a controller configured to:
receive respective images from each camera of the plurality of cameras; and
combine the respective images into a single higher resolution image.

6. The endoscope of claim 1, further comprising a controller configured to:
receive respective images from each camera of the plurality of cameras;
remove dead pixels from the respective images; and
combine the respective images into a single higher resolution image.

7. The endoscope of claim 1, further comprising a controller configured to:
receive respective images from each camera of the plurality of cameras; and
combine the respective images to provide a depth map.

8. The endoscope of claim 1, further comprising a controller configured to:
receive respective images from each camera of the plurality of cameras; and
combine the respective images by using light field processing, whereby a depth map of objects, disposed in front of the plurality of lenses, is provided.

9. The endoscope of claim 1, wherein each respective diameter of the plurality of optical fiber bundles comprises a range of up to approximately 2 mm.

10. The endoscope of claim 1, wherein the common optical element comprises:
a body having a proximal side and distal side, the plurality of lenses formed at the distal side; and
a plurality of respective slots for receiving a respective optical fiber bundle on the proximal side, each respective slot of the plurality of respective slots terminating at a respective lens, of the plurality of lenses, at the distal side.

11. A method of providing an endoscope, the method comprising:
providing a plurality of optical fiber bundles;
providing a plurality of lenses in a one-to-one relationship with the plurality of optical fiber bundles;
providing a plurality of cameras in a one-to-one relationship with the plurality of optical fiber bundles,
each respective optical fiber bundle, of the plurality of optical fiber bundles, having a respective lens, of the plurality of lenses, located at a respective distal end, and a camera, of the plurality of cameras, located at a respective proximal end,
the plurality of optical fiber bundles being coupled together at a common distal end, and otherwise being uncoupled from one another, a bending radius of the endoscope defined by a largest respective bending radius of each of the plurality of optical fiber bundles; and
providing a common optical element, wherein the plurality of lenses are each formed in the common optical element, the common optical element located at the common distal end, the common optical element being one or more of: removable from the common distal end of the plurality of optical fiber bundles; and disposable,
wherein one lens of the plurality of lenses comprises a distinct depth of field and a distinct angle of view in relation to another lens of the of the plurality of lenses.

12. The method of claim 11, wherein the plurality of optical fiber bundles comprises a first optical fiber bundle and a second optical fiber bundle, each optical fiber bundle having the respective lens located at the respective distal end, and the respective camera located at the respective proximal end, thereby forming a three-dimensional camera.

13. The method of claim 11, wherein respective distal ends of the plurality of optical fiber bundles and respective lenses located at the respective distal ends are spaced apart from one another to provide a plurality of distinct views of objects in front of the respective distal ends.

14. The method of claim 11, wherein the one lens of the plurality of lenses further comprises a distinct field of view in relation to the other lens of the of the plurality of lenses.

15. The method of claim 11, further comprising providing a controller configured to:
receive respective images from each camera of the plurality of cameras; and
combine the respective images into a single higher resolution image.

16. The method of claim 11, further comprising providing a controller configured to:
receive respective images from each camera of the plurality of cameras;
remove dead pixels from the respective images; and
combine the respective images into a single higher resolution image.

17. The method of claim 11, further comprising providing a controller configured to:
receive respective images from each camera of the plurality of cameras; and
combine the respective images to provide a depth map.

18. The method of claim 11, further comprising providing a controller configured to:
receive respective images from each camera of the plurality of cameras; and
combine the respective images by using light field processing, whereby a depth map of objects, disposed in front of the plurality of lenses, is provided.

19. The method of claim 11,
wherein each respective diameter of the plurality of optical fiber bundles comprises a range of up to approximately 2 mm, and
wherein the common optical element comprises:
a body having a proximal side and distal side, the plurality of lenses formed at the distal side; and
a plurality of respective slots for receiving a respective optical fiber bundle on the proximal side, each respective slot of the plurality of respective slots terminating at a respective lens, of the plurality of lenses, at the distal side.

20. A method of imaging by way of an endoscope, the method comprising:
providing the endoscope, providing the endoscope comprising:

providing a plurality of optical fiber bundles;
providing a plurality of lenses in a one-to-one relationship with the plurality of optical fiber bundles;
providing a plurality of cameras in a one-to-one relationship with the plurality of optical fiber bundles, each respective optical fiber bundle, of the plurality of optical fiber bundles, having a respective lens, of the plurality of lenses, located at a respective distal end, and a camera, of the plurality of cameras, located at a respective proximal end,
the plurality of optical fiber bundles being coupled together at a common distal end, and otherwise being uncoupled from one another, a bending radius of the endoscope defined by a largest respective bending radius of each of the plurality of optical fiber bundles; and
providing a common optical element, wherein the plurality of lenses are each formed in the common optical element, the common optical element located at the common distal end, the common optical element being one or more of: removable from the common distal end of the plurality of optical fiber bundles; and disposable,
wherein one lens of the plurality of lenses comprises a distinct depth of field and a distinct angle of view in relation to another lens of the of the plurality of lenses;
providing a controller operably coupled with the endoscope; and
operating the endoscope by way of the controller.

* * * * *